United States Patent
Kumagai et al.

(10) Patent No.: US 9,750,394 B2
(45) Date of Patent: Sep. 5, 2017

(54) ENDOSCOPE SYSTEM, ENDOSCOPE APPARATUS, AND PROCESSOR

(71) Applicant: OLYMPUS CORPORATION, Hachioji-shi, Tokyo (JP)

(72) Inventors: Toshihiro Kumagai, Tokyo (JP); Hidenobu Kubo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/143,875

(22) Filed: May 2, 2016

(65) Prior Publication Data
US 2016/0242625 A1    Aug. 25, 2016

Related U.S. Application Data (63) Continuation of application No. PCT/JP2015/066484, filed on Jun. 8, 2015.

(30) Foreign Application Priority Data

Jun. 10, 2014   (JP) .................. 2014-119318

(51) Int. Cl.
*A61B 1/04* (2006.01)
*A61B 1/00* (2006.01)
(Continued)

(52) U.S. Cl.
CPC ...... *A61B 1/00009* (2013.01); *A61B 1/00006* (2013.01); *A61B 1/0008* (2013.01);
(Continued)

(58) Field of Classification Search
CPC ...... G01B 7/02; G02B 23/24; A61B 1/00006; A61B 1/00045; A61B 1/00066; A61B 1/0008; A61B 1/00147
See application file for complete search history.

(56) References Cited

U.S. PATENT DOCUMENTS 3,832,900 A * 9/1974 Ross ................. G01F 23/284
                                                324/643
3,874,237 A * 4/1975 Zwarts ............... G01F 23/284
                                                73/290 R
(Continued)

FOREIGN PATENT DOCUMENTS

JP   2006-043449 A   2/2006
JP   2006-523129 A   10/2006
(Continued)

OTHER PUBLICATIONS

Aug. 25, 2015 Search Report issued in International Patent Application No. PCT/JP2015/066484.
(Continued)

*Primary Examiner* — Anhtuan T Nguyen
*Assistant Examiner* — Jae Woo
(74) *Attorney, Agent, or Firm* — Oliff PLC (57) ABSTRACT

In an endoscope system that obtains a captured image inside of a body cavity by use of an insertion unit of an endoscope apparatus which is inserted into the body cavity of a subject, an oscillator outputs an oscillation pulse signal, and receives a reflected pulse signal. A transmission line is provided along the insertion unit near an envelope of the insertion unit, and transmits a pulse signal output from the oscillator. A time calculating unit and an insertion length calculating unit obtain a time difference between the oscillation pulse signal and the reflected pulse signal on the basis of the oscillation pulse signal output by the oscillator and the reflected pulse signal received by the oscillator, and calculate an insertion length of the insertion unit on the basis of the obtained time difference.

5 Claims, 9 Drawing Sheets

(51) Int. Cl.
*G02B 23/24* (2006.01)
*G01B 7/02* (2006.01)
*A61B 5/06* (2006.01)

(52) U.S. Cl.
CPC ...... *A61B 1/00045* (2013.01); *A61B 1/00066* (2013.01); *A61B 1/00147* (2013.01); *A61B 1/04* (2013.01); *A61B 5/068* (2013.01); *G01B 7/02* (2013.01); *G02B 23/24* (2013.01)

(56) References Cited

U.S. PATENT DOCUMENTS

| | | | | |
|---|---|---|---|---|
| 3,995,212 A * | 11/1976 | Ross | ............... | G01R 27/2664 324/642 |
| 4,559,928 A * | 12/1985 | Takayama | ............ | A61B 1/0052 388/838 |
| 4,633,855 A * | 1/1987 | Baba | ................... | A61B 1/0008 600/117 |
| 4,779,349 A * | 10/1988 | Odensten | ............... | A61B 1/317 33/512 |
| 4,845,555 A * | 7/1989 | Yabe | ................... | H04N 5/23203 348/72 |
| 4,860,095 A * | 8/1989 | Kimura | ..................... | A61B 1/05 348/241 |
| 4,930,494 A * | 6/1990 | Takehana | ............ | A61B 1/00147 600/145 |
| 5,253,647 A * | 10/1993 | Takahashi | ............... | A61B 5/065 600/117 |
| 5,383,366 A * | 1/1995 | Wallingford | ......... | G01N 29/069 73/602 |
| 5,445,144 A * | 8/1995 | Wodicka | ........... | A61M 25/0105 128/207.14 |
| 5,457,394 A * | 10/1995 | McEwan | ............... | G01F 23/284 324/642 |
| 5,656,774 A * | 8/1997 | Nelson | ................... | G01F 23/284 73/290 V |
| 5,728,044 A * | 3/1998 | Shan | ........................ | A61B 1/31 33/512 |
| 5,929,349 A * | 7/1999 | Bass | ...................... | G01B 17/02 33/522 |
| 5,943,908 A * | 8/1999 | Innes | ..................... | G01F 23/284 324/632 |
| 6,178,817 B1 * | 1/2001 | Hewelt | ................. | G01F 23/284 324/637 |
| 6,584,860 B1 * | 7/2003 | Feller | ...................... | G01F 1/106 73/861.25 |
| 6,644,114 B1 * | 11/2003 | McEwan | ............... | G01F 23/284 73/290 R |
| 6,773,394 B2 * | 8/2004 | Taniguchi | ................ | A61B 1/31 600/117 |
| 8,221,308 B2 * | 7/2012 | Noguchi | ................. | A61B 1/31 600/114 |
| 8,343,037 B2 * | 1/2013 | Ishihara | ............. | A61B 1/00147 348/65 |
| 2001/0000851 A1 * | 5/2001 | Morimoto | ............ | G01F 23/266 73/304 C |
| 2004/0049095 A1 * | 3/2004 | Goto | .................. | A61B 1/00098 600/107 |
| 2004/0116775 A1 * | 6/2004 | Taniguchi | ................. | A61B 5/06 600/117 |
| 2004/0176683 A1 * | 9/2004 | Whitin | ..................... | A61B 5/06 600/424 |
| 2006/0009679 A1 | 1/2006 | Ito et al. | | |
| 2006/0293562 A1 * | 12/2006 | Uchimura | ......... | A61B 1/00039 600/110 |
| 2007/0219410 A1 * | 9/2007 | Onoda | ................... | A61B 5/062 600/117 |
| 2007/0249901 A1 * | 10/2007 | Ohline | ................... | A61B 1/005 600/117 |
| 2008/0048669 A1 * | 2/2008 | Scherber | ............... | G01S 13/003 324/534 |
| 2008/0262309 A1 * | 10/2008 | Miyoshi | ............... | A61B 1/0052 600/146 |
| 2009/0209809 A1 * | 8/2009 | Schaller | ................ | A61B 1/018 600/103 |
| 2013/0116679 A1 * | 5/2013 | Van der Weide | .. | A61B 18/1815 606/33 |
| 2013/0190646 A1 * | 7/2013 | Weinstein | ............ | A61B 5/0028 600/547 |
| 2013/0310673 A1 | 11/2013 | Govari et al. | | |
| 2014/0103950 A1 * | 4/2014 | Janitch | ................. | G01F 23/284 324/754.06 |
| 2014/0235962 A1 * | 8/2014 | Yu | .......................... | A61B 8/403 600/301 |
| 2015/0054929 A1 * | 2/2015 | Ito | ......................... | A61B 1/273 348/65 |

FOREIGN PATENT DOCUMENTS

| | | |
|---|---|---|
| JP | 2010-088573 A | 4/2010 |
| JP | 2013-240595 A | 12/2013 |
| WO | 2004/084702 A2 | 10/2004 |

OTHER PUBLICATIONS

Aug. 25, 2015 Written Opinion issued in International Patent Application No. PCT/JP2015/066484.
Nov. 17, 2015 Office Action issued in Japanese Patent Application No. 2015-548523.

* cited by examiner

ENDOSCOPE SYSTEM, ENDOSCOPE APPARATUS, AND PROCESSOR

CROSS-REFERENCE TO RELATED APPLICATIONS

This application is based upon and claims the benefit of priority of the prior Japanese Patent Application No. 2014-119318, filed Jun. 10, 2014, the entire contents of which are incorporated herein by reference.

This is a Continuation Application of PCT Application No. PCT/JP2015/066484, filed Jun. 8, 2015, which was not published under PCT Article 21(2) in English.

BACKGROUND OF THE INVENTION

Field of the Invention

The present invention relates to a technology for calculating an insertion length at which an insertion unit of an endoscope apparatus is inserted into a subject in an endoscope system.

Description of the Related Art

Endoscopy includes upper endoscopy and lower endoscopy. In both the upper endoscopy and the lower endoscopy, when a distal end of an insertion unit of an endoscope apparatus reaches an examination region within a body cavity of a patient who is a subject, an operator of an endoscope starts an examination and various processes relating to the examination. An insertion length (amount) of the endoscope apparatus is generally determined by a doctor who is an operator from an observation image captured by using the endoscope apparatus on the basis of the doctor's experience or the like. Therefore, it may be difficult for an inexperienced resident or the like or a third party to easily grasp a photographed portion (an examination region) by only viewing an observation image.

As a known technology, a technology for observing the shape of an insertion unit of an endoscope apparatus within a body cavity has been proposed. According to this technology, the insertion unit of the endoscope apparatus incorporates a plurality of magnetic coils. A coil unit that is a position detector receives magnetism generated from the plurality of magnetic coils, and as a result, the shape of the insertion unit is obtained. As an example, Japanese Laid-Open Patent Publication No. 2010-88573 discloses a technology for calculating a distance from a position (a base point) in which an insertion unit starts to come into contact with a subject to a distal end of the insertion unit, namely, an insertion length of an endoscope apparatus, by using the technology above.

SUMMARY OF THE INVENTION

It is an object of the present invention to provide a technology that enables an insertion length of an endoscope apparatus to be obtained in an endoscope system having a simple configuration.

An endoscope system according to an aspect of the present invention inserts an insertion unit of an endoscope apparatus into a body cavity of a subject, and obtains a captured image of the body cavity. The endoscope system includes: a pulse oscillator that outputs an oscillation pulse signal; a pulse receiver that receives a reflected pulse signal; a transmission line that is provided along the insertion unit near an envelope of the insertion unit, the transmission line transmitting a pulse signal output from the pulse oscillator; a time calculating unit that obtains a time difference between the oscillation pulse signal and the reflected pulse signal on the basis of the oscillation pulse signal output by the pulse oscillator and the reflected pulse signal received by the pulse receiver; and an insertion length calculating unit that calculates an insertion length of the insertion unit on the basis of the obtained time difference.

Further, an endoscope apparatus according to an aspect of the present invention inserts an insertion unit into a body cavity of a subject, and captures an image inside the body cavity. The endoscope apparatus includes: a pulse oscillator that outputs an oscillation pulse signal; a pulse receiver that receives a reflected pulse signal; and a transmission line that is provided along the insertion unit near an envelope of the insertion unit, the transmission line transmitting a pulse signal output from the pulse oscillator. In the endoscope apparatus, a time difference between the oscillation pulse signal and the reflected pulse signal is obtained on the basis of the oscillation pulse signal output by the pulse oscillator and the reflected pulse signal received by the pulse receiver, and an insertion length of the insertion unit is calculated on the basis of the obtained time difference.

Furthermore, a processor according to an aspect of the present invention processes a video signal of an inside of a body cavity of a subject, the video signal being obtained by imaging the inside of the body cavity of the subject by using an endoscope apparatus. The processor includes: a time calculating unit that obtains a time difference between an oscillation pulse signal and a reflected pulse signal on the basis of the oscillation pulse signal output by a pulse oscillator and the reflected pulse signal received by a pulse receiver, the oscillation pulse signal and the reflected pulse signal being received from the endoscope apparatus including the pulse oscillator, the pulse receiver, and a transmission line, the pulse oscillator outputting the oscillation pulse signal, the pulse receiver receiving the reflected pulse signal, the transmission line being provided along an insertion unit near an envelope of the insertion unit and transmitting a pulse signal output from the pulse oscillator; and an insertion length calculating unit that calculates an insertion length of the insertion unit on the basis of the obtained time difference.

BRIEF DESCRIPTION OF THE DRAWINGS

The present invention will be more apparent from the following detailed description when the accompanying drawings are referenced.

DESCRIPTION OF THE PREFERRED EMBODIMENTS

Embodiments of the present invention are described below in detail with reference to the drawings.

Figure 1:
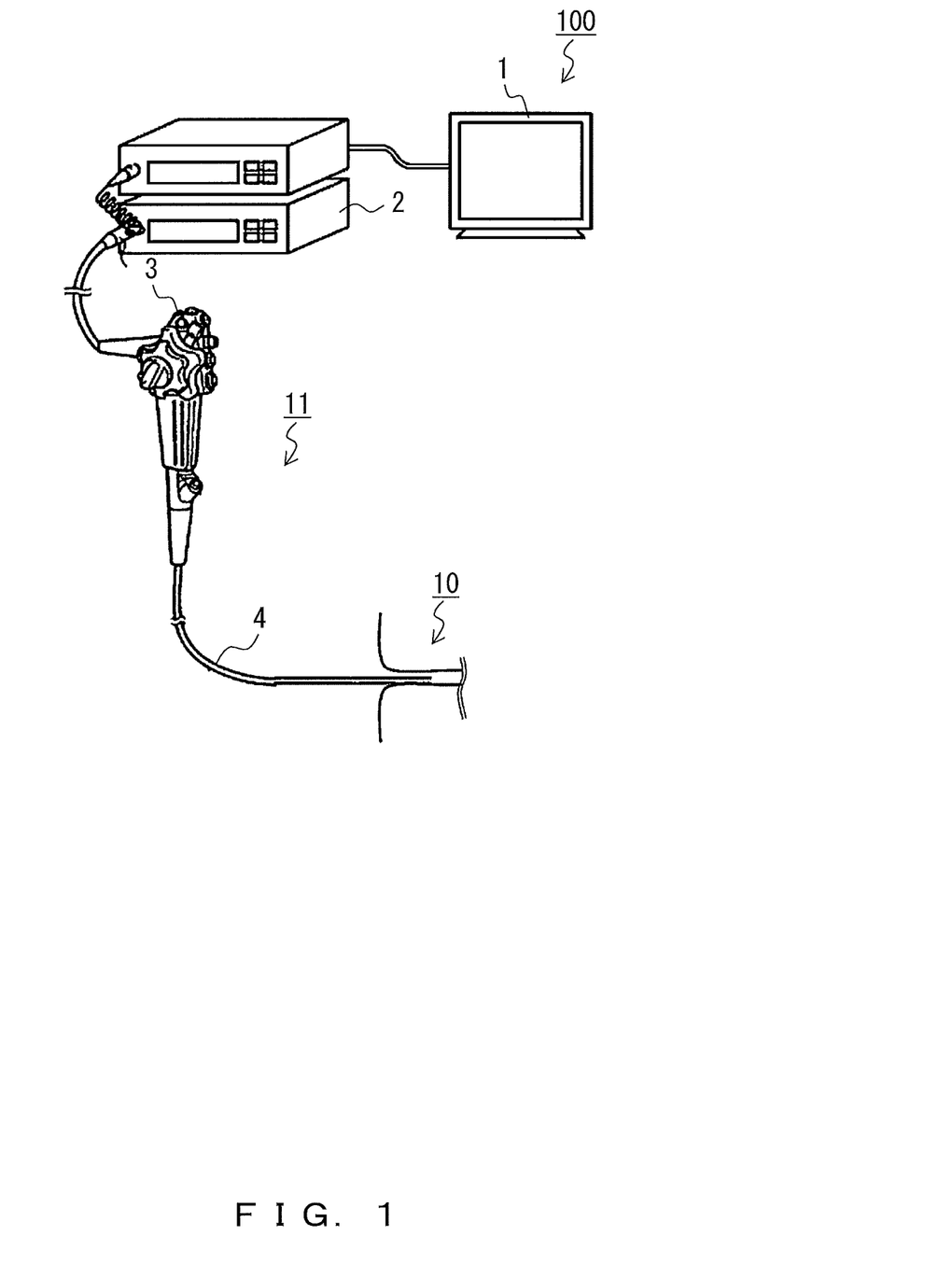
FIG. 1 illustrates a configuration of an endoscope system according to an embodiment.

FIG. 1 illustrates a configuration of an endoscope system according to an embodiment. An endoscope system 100 illustrated in FIG. 1 includes an endoscope apparatus (scope) 11, a processor 2, and a monitor 1. By using the endoscope system 100, a doctor who is an operator of the endoscope apparatus 11 obtains an image inside a body cavity 10 of a patient who is a subject, and performs endoscopy or the like. In FIG. 1 and the drawings that follow, a case in which lower endoscopy is performed by using a lower gastrointestinal tract endoscope apparatus is explained as an example.

The endoscope apparatus 11 includes an insertion unit 4 and an operation unit 3. An imaging unit provided at a distal end of the insertion unit 4 captures an image inside the body cavity 10 of a subject, and transmits an obtained video signal to the processor 2. The operation unit 3 receives various operations performed by a doctor, such as a release operation, and transmits operation instruction signals according to the received operations to the processor 2. In the embodiment, the operation unit 3 includes an oscillator and a receiver used to obtain an insertion length at which the insertion unit 4 is inserted into a body cavity of a subject, and the operation unit 3 detects an output timing and a reception timing of a pulse signal output from the oscillator. This will be described later in detail.

The processor 2 controls the endoscope apparatus 11 in accordance with a signal input from the operation unit 3 of the endoscope apparatus 11. The processor 2 also performs necessary image processing on a video signal input from the endoscope apparatus 11, and transmits obtained image data to the monitor 1. In this case, in the embodiment, the processor obtains, from the endoscope apparatus 11, information relating to the output timing and the reception timing of the pulse signal described above in the endoscope apparatus 11. The processor 2 then calculates an insertion length of the insertion unit 4 of the endoscope apparatus 11 on the basis of the obtained information, and transmits the insertion length together with corresponding image data to the monitor 1.

The monitor 1 displays the image inside the body cavity of the subject on the basis of the image data input from the processor 2. In a case in which the data input from the processor 2 includes data of the insertion length of the insertion unit 4, the monitor 1 displays the insertion length in addition to an endoscopic image.

As described above, in the endoscope system 100 illustrated in FIG. 1, the processor 2 calculates the insertion length of the insertion unit 4 of the endoscope apparatus 11 on the basis of information obtained from the endoscope apparatus 11, and displays the insertion length in addition to a corresponding image on the monitor 1. Specific structures and actions of the endoscope apparatus 11 and the processor 2 used to obtain the insertion length of the insertion unit 4 in the endoscope system 100 are described below in detail.

Figure 2:
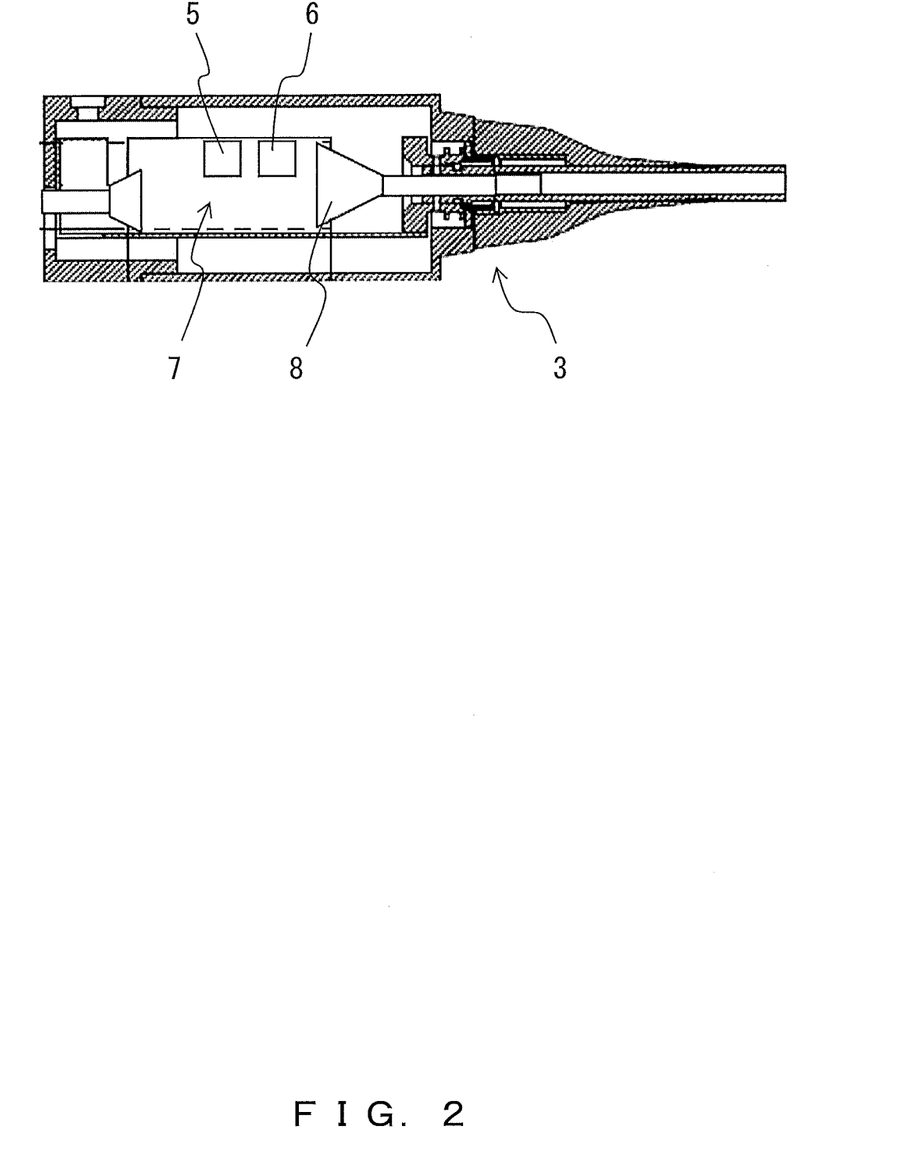
FIG. 2 illustrates a structure of an operation unit of an endoscope apparatus according to an embodiment.

FIG. 2 illustrates a structure of the operation unit 3 of the endoscope apparatus 11 according to the embodiment. As illustrated in FIG. 2, the operation unit 3 of the endoscope apparatus 11 according to the embodiment includes an oscillator 5 and a sample-and-hold circuit 6 on a board 7, and the sample-and-hold circuit 6 includes an amplifier/filter 8.

The oscillator 5 outputs an oscillation pulse signal. The sample-and-hold circuit 6 samples a voltage waveform of an output unit of the oscillator 5. The pulse signal output from the oscillator 5 is transmitted in the insertion unit 4 through a transmission line, and returns to the oscillator 5.

Figures 3A, 3B:
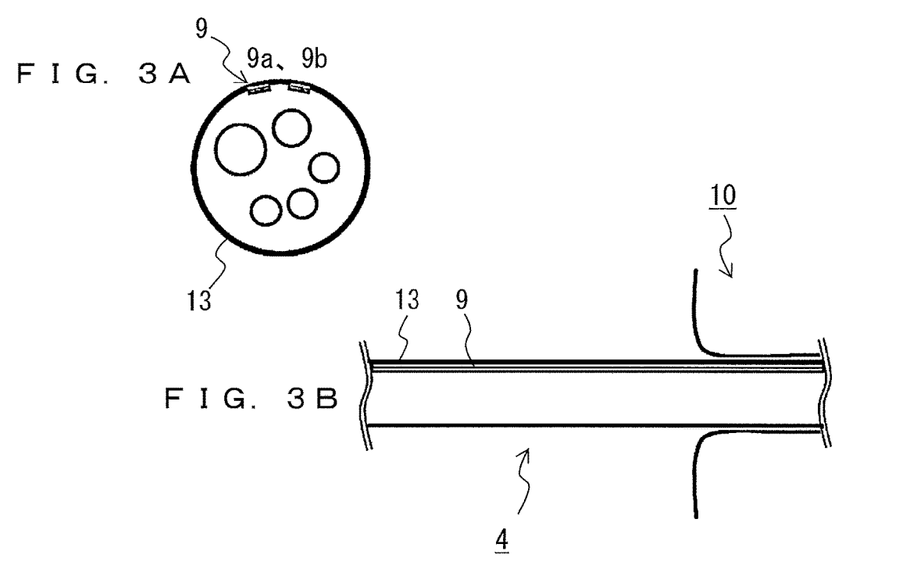
FIG. 3A illustrates a transmission line arranged in an insertion unit of an endoscope apparatus according to an embodiment.
FIG. 3B illustrates a transmission line arranged in an insertion unit of an endoscope apparatus according to an embodiment.

FIGS. 3A and 3B illustrate a transmission line arranged in the insertion unit 4 of the endoscope apparatus 11 according to the embodiment. FIG. 3A is a sectional view in a direction vertical with respect to an insertion direction of the insertion unit 4, and FIG. 3B is a sectional view in a direction parallel with respect to the insertion direction.

As illustrated in FIGS. 3A and 3B, the insertion unit 4 of the endoscope apparatus 11 according to the embodiment includes a transmission line 9 (9a or 9b) arranged along the insertion unit 4 near an envelope 13 of the insertion unit 4. As described above, an oscillation pulse signal output from the oscillator 5 illustrated in FIG. 2 is transmitted to a distal end of the insertion unit 4 through the transmission line 9 (9a), and a reflected pulse signal returns to the oscillator 5 through the transmission line 9 (9b). The sample-and-hold circuit 6 arranged in the operation unit 3 together with the oscillator samples the voltage waveform of the output unit of the oscillator 5 so as to detect a timing at which the oscillation pulse signal is output from the oscillator 5 and a timing at which the reflected pulse signal returns to the oscillator 5.

The processor 2 controls the oscillator 5 and the sample-and-hold circuit 6 provided in the operation unit 3 so as to obtain a result of sampling in the sample-and-hold circuit 6, calculate the insertion length of the insertion unit 4, and output the insertion length to a device outside the processor 2, such as the monitor 1.

Figure 4:
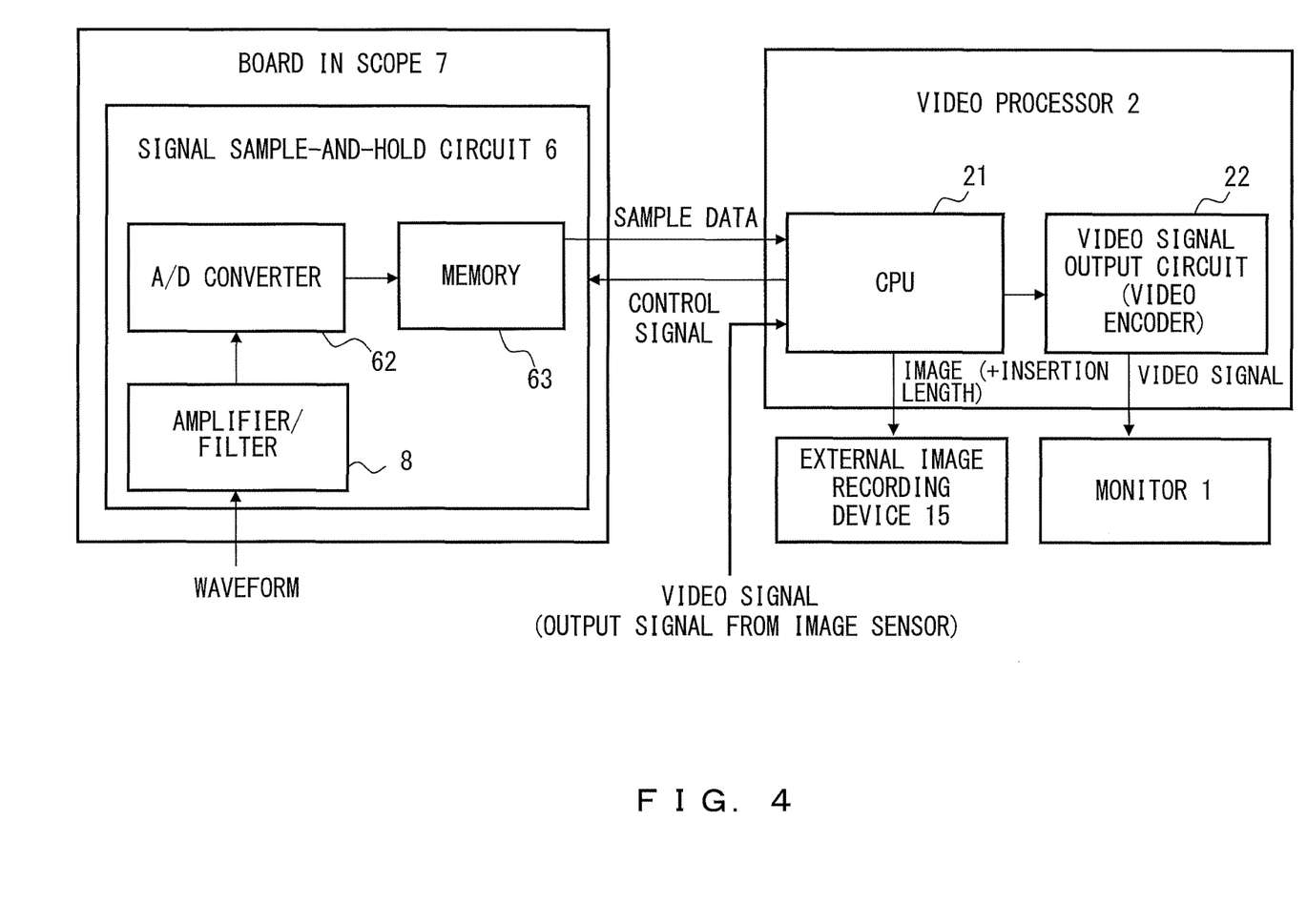
FIG. 4 is a block diagram illustrating the configuration of an endoscope system according to an embodiment.

FIG. 4 is a block diagram illustrating the configuration of the endoscope system 100 according to the embodiment. FIG. 4 principally illustrates a configuration relating to the calculation of the insertion length of the insertion unit 4 of the endoscope apparatus 11.

In the endoscope system 100 illustrated in FIG. 4, the sample-and-hold circuit 6 in the board 7 of the endoscope apparatus 11 includes the amplifier/filter 8, an A/D converter 62, and a memory 63. The processor 2 includes a CPU 21 and a video signal output circuit 22.

The amplifier/filter 8 of the sample-and-hold circuit 6 corrects a waveform on the transmission line 9 of the insertion unit 4. The A/D converter 62 performs A/D conversion on the waveform input from the amplifier/filter 8 so as to obtain a pulse signal. The memory 63 stores digital data of the pulse signal obtained by the A/D converter 62.

The CPU 21 of the processor 2 reads data that has been stored in the memory 63 of the sample-and-hold circuit 6 provided on the board 7 of the operation unit 3 of the endoscope apparatus 11. The CPU 21 calculates the insertion length of the insertion unit 4 by using the data read from the memory 63 of the sample-and-hold circuit 6. The configuration and actions of the CPU 21 are described later in more detail with reference to FIG. 5 and the like. The CPU 21 performs necessary processing on a video signal output from an image sensor of the endoscope apparatus 11, and outputs obtained image data with data of the calculated insertion length associated (superimposed). An output destination is the monitor 1 or an external image recording device 15 in the embodiment.

In a case in which the output destination of data is the external image recording device 15, the external image recording device 15 records the data of the insertion length in the received superimposed data, in association with the image data.

In a case in which the output destination of data is the monitor 1, a video signal output circuit 22 configured of a video encoder or the like generates image data to be displayed on the monitor 1 on the basis of the data input from the CPU 21, namely, the data obtained by superimposing the data of the insertion length onto the image data. Then, the video signal output circuit 22 outputs the generated image data to the monitor 1. The monitor 1 displays an endoscopic image, and an image including the insertion length of the insertion unit 4 that corresponds to the endoscopic image, on the basis of the image data received from the processor 2.

In the description above, the CPU 21 calculates an insertion length by reading and executing a program recorded in a memory (not illustrated) or the like of the processor 2. However, the configuration above does not always need to be employed, and a configuration may be employed in which an FPGA (field-programmable gate array) or the like implements the above process for calculating an insertion length.

Figure 5:
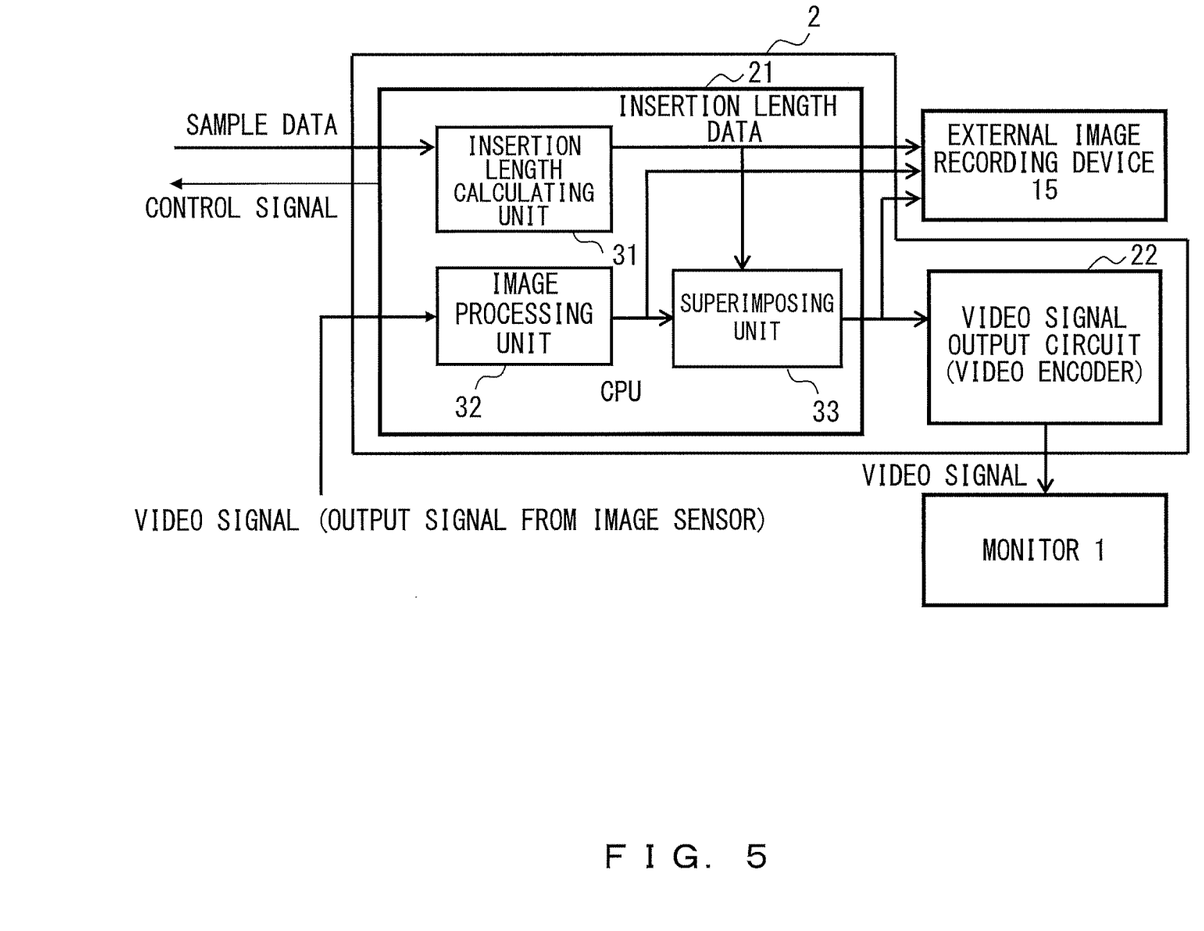
FIG. 5 is a functional block diagram of a CPU (or an FPGA) of a video processor according to an embodiment.

FIG. 5 is a functional block diagram of the CPU 21 (or the FPGA) of the video processor 2 according to the embodiment. The CPU 21 (or the FPGA) illustrated in FIG. 5 includes an insertion length calculating unit 31, an image processing unit 32, and a superimposing unit 33. FIG. 5 only illustrates a configuration relating to the calculation and output of the insertion length of the insertion unit 4 of the endoscope apparatus 11.

The insertion length calculating unit 31 reads data from the memory 63 of the sample-and-hold circuit 6, and obtains the insertion length of the insertion unit 4 on the basis of the read data. The insertion length calculating unit 31 calculates the insertion length of the insertion unit 4 on the basis of a fact that the insertion length of the insertion unit 4 is determined according to a time difference after the operation unit 3 outputs an oscillation pulse signal and before the operation unit 3 receives a reflected pulse signal. This is described below with reference to FIGS. 6A, 6B, 7A, and 7B.

Figure 6A:
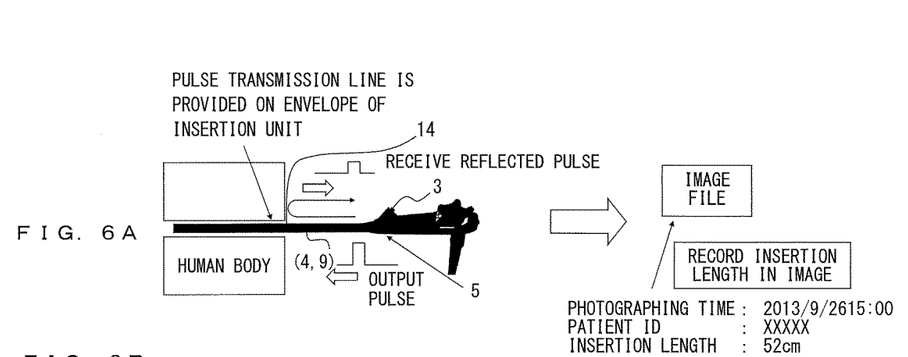
FIG. 6A is a diagram explaining a principle for calculating an insertion length of an insertion unit of an endoscope apparatus by using an oscillation pulse signal and a reflected pulse signal.
Figure 6B:
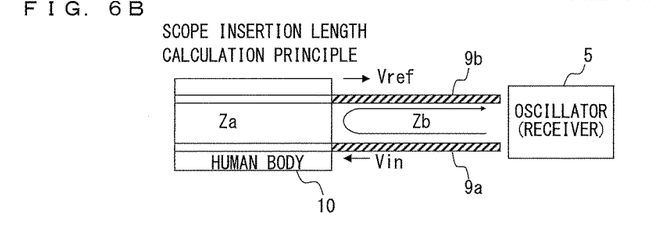
FIG. 6B is a diagram explaining a principle for calculating an insertion length of an insertion unit of an endoscope apparatus by using an oscillation pulse signal and a reflected pulse signal.

FIGS. 6A and 6B are diagrams explaining a principle for calculating the insertion length of the insertion unit 4 of the endoscope apparatus 11 by using an oscillation pulse signal and a reflected pulse signal.

A dielectric constant differs between the inside of the human body and the outside of the human body (namely, in the air). Because the dielectric constant differs between the inside and the outside of the human body, a characteristic impedance of the transmission line 9 also differs between a region inside the human body (in a body cavity) and a region outside the human body. Therefore, as illustrated on a left-hand side of FIG. 6A, when the insertion unit 4 of the endoscope apparatus 11 is inserted into a body cavity of a subject, an oscillation pulse signal that has been output from the oscillator 5 provided in the operation unit 3 is not transmitted to the inside of the human body, is reflected in a position 14 in which the subject starts to come into contact with the insertion unit 4, and returns to the operation unit 3.

As described above, in the endoscope system 100 according to the embodiment, a time period during which a pulse signal is transmitted through the transmission line 9 in a region outside the human body (a region that has not been inserted into a body cavity) from among the entirety of the region of the insertion unit 4 is calculated by using the time domain reflectometry (TDR). Specifically, the output of an oscillation pulse signal and the reception of a reflected pulse signal in the oscillator 5 are detected by the sample-and-hold circuit 6, a time difference between the output and the reception is obtained, and an uninserted length of the insertion unit 4 is calculated on the basis of the obtained time difference.

Assume that voltages of the oscillation pulse signal and the reflected pulse signal detected by the sample-and-hold circuit 6 are Vin and Vref, respectively, as illustrated in FIG. 6B. A ratio of the voltage of the reflected pulse signal to the voltage of the oscillation pulse signal is represented by Expression (1) described below. In Expression (1), Za and Zb are characteristic impedances of the transmission line 9 inside and outside the human body, respectively.

$$\text{(Pulse reflectance)} = V_{ref}/V_{in} = (Za-Zb)/(Za+Zb) \quad (1)$$

In a case in which a pulse signal having a sharp edge, such as a pulse wave or a step wave, is transmitted from the oscillator 5, a waveform detected by the sample-and-hold circuit 6 differs between an incident voltage waveform (a waveform of an oscillation pulse signal) and a reflected voltage waveform (a waveform of a reflected pulse signal). In the embodiment, the sample-and-hold circuit 6 performs sampling by using this difference so as to detect an output timing of an oscillation pulse signal and a reception timing of a reflected pulse signal.

Figure 7A:
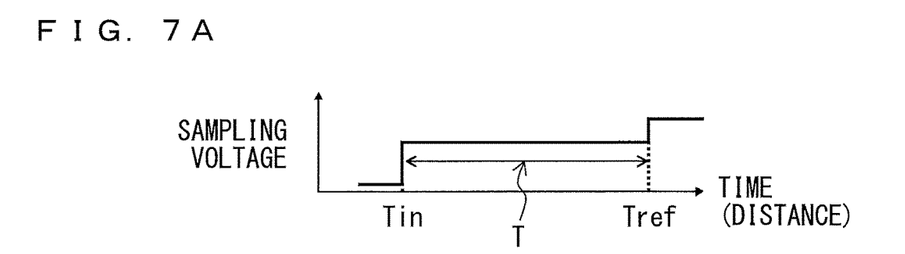
FIG. 7A is a diagram explaining a voltage of a pulse signal detected by a sample-and-hold circuit.
Figure 7B:
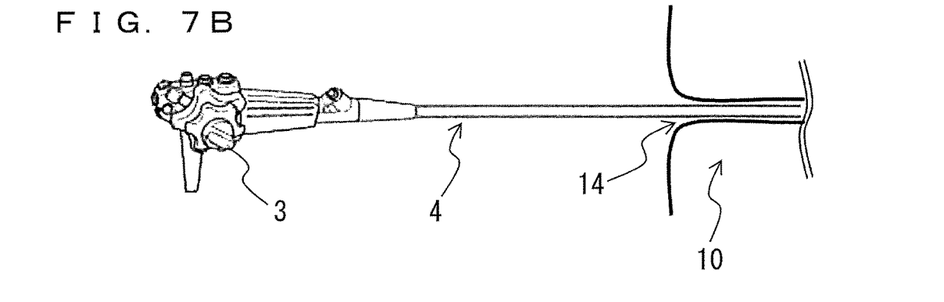
FIG. 7B is a diagram explaining a voltage of a pulse signal detected by a sample-and-hold circuit.

FIGS. 7A and 7B are diagrams explaining a voltage of a pulse signal detected by the sample-and-hold circuit 6.

FIG. 7A schematically illustrates a change in a voltage detected by (the operation unit 3 of) the endoscope apparatus 11 according to the embodiment. Specifically, FIG. 7A illustrates a change in a voltage value of a pulse signal output from the A/D converter 62 illustrated in FIG. 4.

As represented by Expression (1) above, a voltage ratio Vref/Vin of a reflected pulse signal to an oscillation pulse signal depends on the characteristic impedances Za and Zb of the transmission line 9 inside and outside the human body, namely, the insertion length of the insertion unit 4 of the endoscope apparatus 11. As described with reference to FIGS. 6A and 6B, the length of an uninserted region of the insertion unit 4 depends on a time difference ($T=T_{ref}-T_{in}$) after the operation unit 3 outputs an oscillation pulse signal and before the operation unit 3 receives a reflected pulse signal.

As illustrated in FIG. 7B, when the insertion unit 4 of the endoscope apparatus 11 continues to be inserted into a subject, a length from the operation unit 3 to the position 14 (the length of an uninserted region) gradually decreases. Accordingly, a time difference T from a timing ($T_{in}$) at which an oscillation pulse signal is detected to a timing ($T_{ref}$) at which a reflected pulse signal is received also decreases. Before endoscopy is started, a pulse signal is transmitted over the entire length of the insertion unit 4, and therefore a time $T_0$ needed to transmit the pulse signal over the entire length of the insertion unit 4 is obtained. Thus, in the CPU 21 (or the FPGA) of the processor 2, the insertion length calculating unit 31 first calculates the time difference T above obtained for a pulse signal output at a certain timing. The insertion length calculating unit 31 then calculates the insertion length of the insertion unit 4 at this timing on the basis of the time $T_0$ needed to transmit the pulse signal over the entire length of the insertion unit 4, the entire length of the insertion unit 4, and the calculated time T.

Specifically, a ratio of the length of an uninserted region of the insertion unit 4 to the entire length of the insertion unit 4 corresponds to a ratio of a time T to a time $T_0$ measured when insertion length=0 is established. The time $T_0$ when insertion length=0 is established can be measured, for example, before endoscopy is started. The length of the uninserted region obtained as above is subtracted from the entire length so as to calculate the insertion length. Assume that the entire length of the insertion unit 4 is L. The insertion length of the insertion unit 4 is obtained according to Expression (2) described below.

$$\text{(Insertion length of insertion unit 4)} = L - (T/T_0) \times L \quad (2)$$

Return now to the description of FIG. 5. The image processing unit 32 performs necessary processing on a video signal output from an image sensor at the distal end of the endoscope apparatus 11. Details of image processing performed by the image processing unit 32 are omitted here because the image processing is performed by using a known technology.

The superimposing unit 33 superimposes data of an insertion length obtained by the insertion length calculating unit 31 onto the video signal obtained by the image processing unit 32, and outputs the superimposed data to the external image recording device 15 or the video signal output circuit 22 in the processor 2. In this case, two pieces of data to be superimposed, namely, a video signal relating to an endoscopic image obtained as a result of a process of the image processing unit 32 and data of the insertion length obtained by the insertion length calculating unit 31 need to correspond to each other. A method in which the processor 2 obtains the insertion length of the insertion unit 4 of the endoscope apparatus 11 at a certain point in time on the basis of data obtained by (the operation unit 3 of) the endoscope apparatus 11, and outputs the insertion length, together with a video signal obtained by imaging at the point in time, to the outside is described with reference to FIG. 8.

Figure 8:
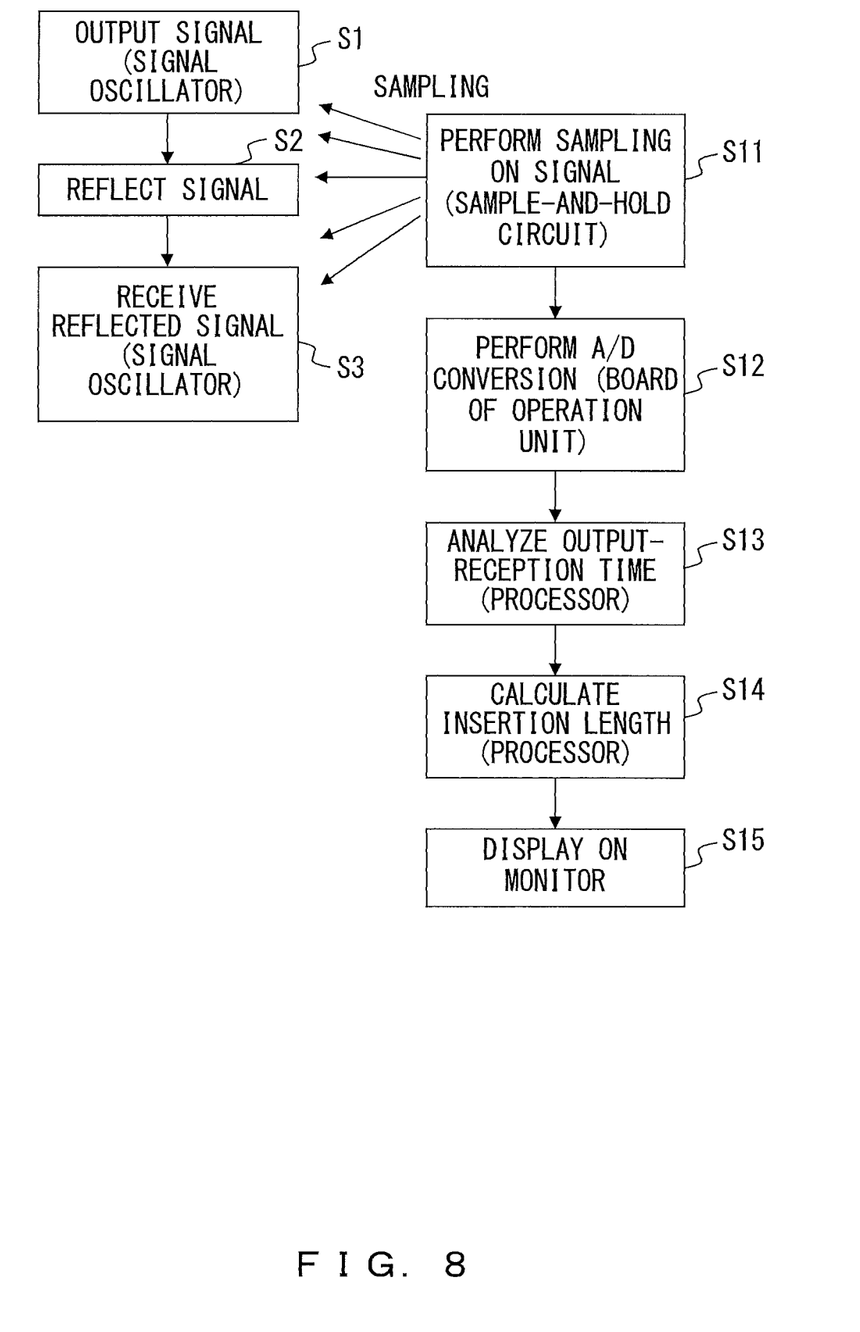
FIG. 8 is a flowchart illustrating processing relating to the calculation of an insertion length of an insertion unit of an endoscope apparatus in an endoscope system according to an embodiment.

FIG. 8 is a flowchart illustrating processing relating to the calculation of the insertion length of the insertion unit 4 of the endoscope apparatus 11 in the endoscope system 100 according to the embodiment. FIG. 8 illustrates a case in which an output destination of data of a calculated insertion length (and data of an associated endoscopic image) is the monitor 1. In FIG. 8, a processing flow relating to a pulse signal on the side of the operation unit 3 of the endoscope apparatus 11 and a processing flow that is performed by the CPU 21 of the processor 2 in accordance with a pulse signal that the operation unit 3 outputs and receives are illustrated separately.

When the oscillator 5 of the operation unit 3 outputs an oscillation pulse signal at a certain timing (step S1), the sample-and-hold circuit 6 starts sampling (step S11). A pulse signal is transmitted through the transmission line 9 in the insertion unit 4, is reflected by a subject (step S2), and returns to the oscillator 5 through the transmission line 9 (step S3). Consequently, the sample-and-hold circuit 6 of the operation unit 3 detects the oscillation pulse signal that has been output in step S1 and a reflected pulse signal that corresponds to the oscillation pulse signal.

When the sample-and-hold circuit 6 on the board 7 detects a waveform, the A/D converter 62 of the sample-and-hold circuit 6 performs A/D conversion on the input waveform (after the amplifier/filter 8 performs amplification or filtering as needed) (step S12). The A/D converter 62 stores digital data of a reflected pulse signal obtained as a result of the A/D conversion in the memory 63.

In the processor 2, the insertion length calculating unit 31 of the CPU 21 reads the digital data of the pulse signal from the memory 63 of the sample-and-hold circuit 6, and analyzes and calculates the time T illustrated in FIGS. 7A and 7B after the oscillation pulse signal is output and before the reflected pulse signal is received on the basis of the digital data (step S13). Because the waveform of the oscillation pulse signal is different from the waveform of the reflected pulse signal, as described above, the insertion length calculating unit 31 uses this difference so as to determine an output timing ($T_{in}$) of the oscillation pulse signal and a reception timing ($T_{ref}$) of the reflected pulse signal on the basis of the digital data. Then, the insertion length calculating unit 31 calculates a time difference T ($=T_{ref}-T_{in}$) between the output timing ($T_{in}$) and the reception timing ($T_{ref}$).

The insertion length calculating unit 31 of the CPU 21 substitutes the obtained time T in Expression (2) above so as to calculate the insertion length of the insertion unit 4 (step S14).

The CPU 21 superimposes the data of the insertion length obtained by the superimposing unit 33 onto the data of the endoscopic image. As in the example illustrated in FIG. 8, in a case in which an output destination of the superimposed data is the monitor 1, the video signal output circuit 22 generates composite image data obtained by composing the data of the endoscopic image and the data of the insertion length on the basis of the superimposed data, and outputs the composite image data to the monitor 1. The monitor 1 displays the insertion length of the insertion unit 4 of the endoscope apparatus 11 in addition to the endoscopic image on the basis of the received composite image data (step S15), and the process is terminated.

Figure 9:
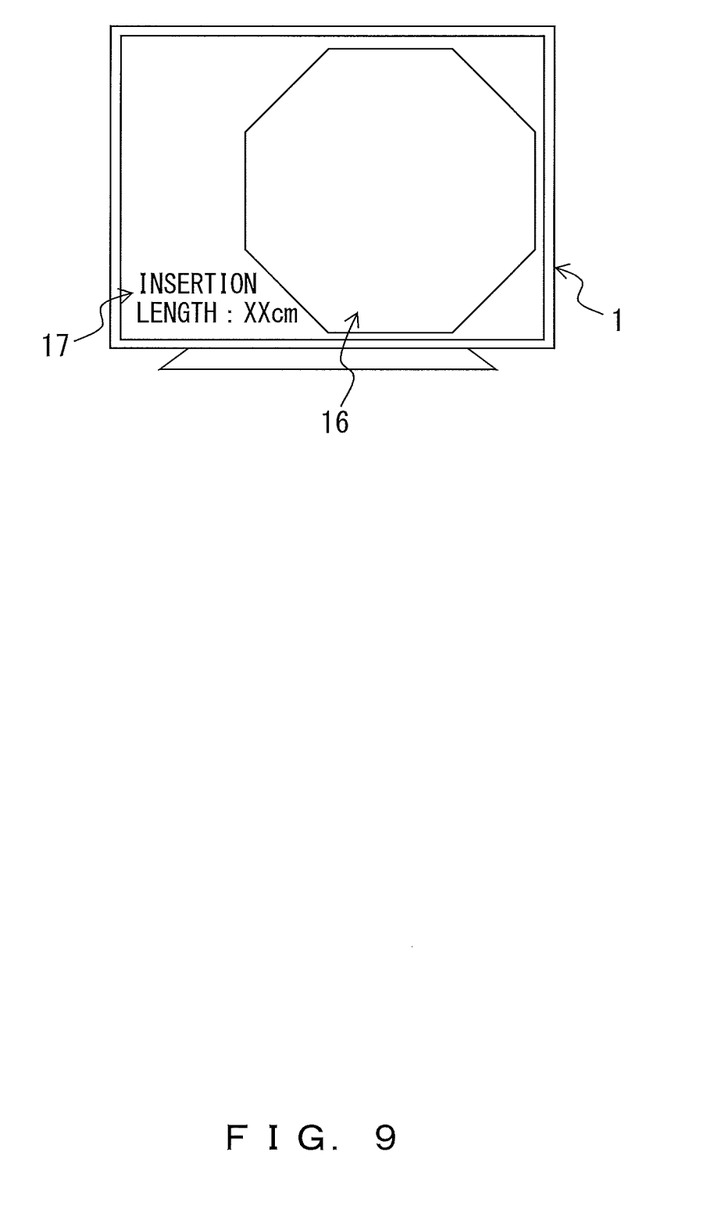
FIG. 9 illustrates a screen displayed on a monitor.

FIG. 9 illustrates a screen displayed on the monitor 1. As illustrated in FIG. 9, a screen including an endoscopic image 16 and an insertion length 17 of the insertion unit 4 when the endoscopic image is captured is displayed on the monitor 1.

In step S15 of FIG. 8, an obtained insertion length together with a corresponding endoscopic image is displayed on the monitor 1, but the present invention is not limited to this. As an example, data of an insertion length and corresponding image data are recorded in the external image recording device 15 in association with each other.

As an example, in lower endoscopy, the large intestine is generally divided into three regions such as the descending colon, the transverse colon, or the ascending colon, and endoscopy is performed on the respective three examination regions. The three regions do not have peculiar characteristics such as shape or color of an organ. Therefore, it is difficult to specify which region an examination image represents by only viewing an endoscopic image. A doctor or the like can easily specify an examination region, for example, by displaying or recording an endoscopic image in association with an insertion length.

In upper endoscopy, the insertion unit 4 starts to come into contact with a subject in an entrance portion of the esophagus. Therefore, in a case in which the method above is employed in upper endoscopy, an insertion length from the entrance portion of the esophagus can be obtained.

As described above, in the endoscope system 100 according to the embodiment, a pulse signal output from an oscillator is transmitted through the transmission line 9 provided along the insertion unit 4 near an envelope of the insertion unit 4 of the endoscope apparatus 11. The transmitted pulse signal is reflected in the position 14 in which the insertion unit 4 comes into contact with a subject, and returns to the oscillator 5. The sample-and-hold circuit 6 detects an oscillation pulse signal and a reflected pulse signal, and obtains a time difference between the oscillation pulse signal and the reflected pulse signal. By using a fact that the obtained time difference is determined according to the length of an uninserted region of the insertion unit 4, the length of the uninserted region is subtracted from the entire length L of the insertion unit 4 so as to calculate the insertion length of the insertion unit 4. The insertion length of the endoscope apparatus 11 can be calculated by using a simple configuration with no need for a large-scale apparatus.

A timing at which an oscillation pulse signal is output from the oscillator 5 in step S1 of FIG. 8 is controlled by the CPU 21 of the processor 2. Therefore, a timing at which a series of processes illustrated in FIG. 8 are started may be, for example, a timing at which a doctor depresses a release button provided in the operation unit 3 and the processor 2 receives a release instruction. In this case, an oscillation pulse signal is output in response to the release instruction, and the sample-and-hold circuit 6 detects an output timing of the oscillation pulse signal and a reception timing of a reflected pulse signal, and calculates the insertion length of the insertion unit 4 on the basis of the output timing and the reception timing by using the method above. In the configuration described above, an insertion length of an examination region at a timing of a release operation, namely, a portion that the doctor suspects to be a lesion, is recorded or displayed, for example. Consequently, a region that the doctor suspects to be a lesion can be easily specified, in particular, when a report is generated after an examination.

Alternatively, a configuration may be employed in which an oscillation pulse signal is periodically output and the insertion length of the insertion unit 4 is periodically calculated by using the oscillation pulse signal. In this case, a series of processes illustrated in FIG. 8 are periodically performed, a reflected pulse signal that corresponds to each of the periodically output oscillation pulse signals is detected, and a time difference T between each of the oscillation signals and the corresponding reflected pulse signal is obtained so as to calculate the insertion length. The calculated insertion length is associated with an endoscope image that corresponds to a timing at which each of the oscillation pulse signals is output. By employing the configuration above, for example, during an examination, a doctor can easily specify which examination region an endoscopic image displayed on the monitor 1 represents without performing a special operation.

Further, the embodiment above has been described using, as an example, a case in which an oscillator and a receiver are provided in the operation unit 3 of the endoscope apparatus 11. The oscillator and the receiver are provided in the operation unit 3 so that the quality of a waveform of a received reflected pulse signal can be prevented from deteriorating as far as possible. As described above, it is preferable from the viewpoint of precision that the oscillator and the receiver be provided in the operation unit 3, but the configuration above does not always need to be employed in order to implement a method for calculating the insertion length of the insertion unit of the endoscope apparatus 11 according to the embodiment. As an example, a configuration may be employed in which the oscillator and the receiver (in addition to the sample-and-hold circuit) are provided in the processor 2.

The present invention is not limited to the embodiment above, and various embodiments can be realized by modifying components without departing from the scope of the present invention. In addition, various inventions can be implemented by appropriately combining a plurality of components disclosed in the embodiment above. As an example, all of the components disclosed in the embodiment may be appropriately combined. Further, some components disclosed in different embodiments may be appropriately combined. Of course, various variations or applications can be made without departing from the spirit of the invention.

What is claimed is:

1. An endoscope system that obtains a captured image inside a body cavity while an insertion unit of an endoscope apparatus is inserted into a subject, the endoscope system comprising:
   a pulse oscillator that outputs an oscillation pulse signal, the pulse oscillator outputs the oscillation pulse signal in response to a release instruction received by an operation unit of the endoscope apparatus;
   a pulse receiver that receives a reflected pulse signal;
   a transmission line that is provided along the insertion unit near an envelope of the insertion unit, the transmission line transmitting the oscillation pulse signal output from the pulse oscillator; and
   a processor programmed to:
      obtain a time difference between the oscillation pulse signal and the reflected pulse signal based on the oscillation pulse signal output by the pulse oscillator and the reflected pulse signal received by the pulse receiver;
      calculate an insertion length of the insertion unit based on the obtained time difference, the insertion length of the insertion unit being calculated by using the oscillation pulse signal output in response to the release instruction; and
      output the calculated insertion length of the insertion unit, to an outside, together with a captured image obtained in response to the release instruction, in association with the captured image.

2. The endoscope system according to claim 1, wherein the pulse oscillator and the pulse receiver are provided in the operation unit of the endoscope apparatus.

3. An endoscope system that obtains a captured image inside a body cavity while an insertion unit of an endoscope apparatus is inserted into a subject, the endoscope system comprising:
   a pulse oscillator that periodically outputs an oscillation pulse signal;
   a pulse receiver that receives a reflected pulse signal;
   a transmission line that is provided along the insertion unit near an envelope of the insertion unit, the transmission line transmitting the oscillation pulse signal output from the pulse oscillator; and
   a processor programmed to:
      obtain a time difference between the oscillation pulse signal and the reflected pulse signal based on the oscillation pulse signal output by the pulse oscillator and the reflected pulse signal received by the pulse receiver; and
      calculate an insertion length of the insertion unit based on the obtained time difference; and
      output, to an outside, the calculated insertion length of the insertion unit in association with the captured image, the calculated insertion length being output by using each of the oscillation pulse signals that are periodically output, together with a captured image obtained at a timing that corresponds to each of the oscillation pulse signals, in association with the captured image.

4. A processor that processes a video signal of an inside of a subject, the video signal being obtained by imaging the inside of the subject by using an endoscope apparatus, the processor comprising:
- a time calculating unit that obtains a time difference between an oscillation pulse signal and a reflected pulse signal based on the oscillation pulse signal output by a pulse oscillator and the reflected pulse signal received by a pulse receiver, the oscillation pulse signal and the reflected pulse signal being received from the endoscope apparatus including the pulse oscillator, the pulse receiver, and a transmission line, the pulse oscillator outputting the oscillation pulse signal, the pulse receiver receiving the reflected pulse signal, the transmission line being provided along an insertion unit near an envelope of the insertion unit and transmitting a pulse signal output from the pulse oscillator;
- an insertion length calculating unit that calculates an insertion length of the insertion unit based on the obtained time difference; and
- an output unit that outputs the calculated insertion length of the insertion unit, to an outside, together with a captured image obtained in response to a release instruction, in association with the captured image, wherein:
  - the pulse oscillator outputs the oscillation pulse signal in response to the release instruction received by an operation unit of the endoscope apparatus; and
  - the time calculating unit calculates the insertion length of the insertion unit by using the oscillation pulse signal output in response to the release instruction.

5. A processor that processes a video signal of an inside of a subject, the video signal being obtained by imaging the inside of the subject by using an endoscope apparatus, the processor comprising:
- a time calculating unit that obtains a time difference between an oscillation pulse signal and a reflected pulse signal based on the oscillation pulse signal output by a pulse oscillator and the reflected pulse signal received by a pulse receiver, the oscillation pulse signal and the reflected pulse signal being received from the endoscope apparatus including the pulse oscillator, the pulse receiver, and a transmission line, the pulse oscillator periodically outputting the oscillation pulse signal, the pulse receiver receiving the reflected pulse signal, the transmission line being provided along an insertion unit near an envelope of the insertion unit and transmitting a pulse signal output from the pulse oscillator;
- an insertion length calculating unit that calculates an insertion length of the insertion unit based on the obtained time difference; and
- an output unit that outputs, to an outside, the calculated insertion length of the insertion unit in association with the captured image, the calculated insertion length being output by using each of the oscillation pulse signals that are periodically output, together with a captured image obtained at a timing that corresponds to each of the oscillation pulse signals, in association with the captured image.

* * * * *